(12) United States Patent
Richard et al.

(10) Patent No.: US 8,747,816 B2
(45) Date of Patent: Jun. 10, 2014

(54) UV-PHOTOPROTECTIVE COMPOSITIONS COMPRISING DIEBENZOYLMETHANE SCREENING AGENTS AND SILICON-CONTAINING S-TRIAZINE COMPOUNDS SUBSTITUTED WITH TWO AMINOBENZOATE OR AMINOBENZAMIDE GROUPS

(75) Inventors: Herve Richard, Les Pavillons Sous Bois (FR); Didier Candau, Bievres (FR)

(73) Assignee: L'Oreal, Paris (FR)

( * ) Notice: Subject to any disclaimer, the term of this patent is extended or adjusted under 35 U.S.C. 154(b) by 1039 days.

(21) Appl. No.: 11/998,421

(22) Filed: Nov. 30, 2007

(65) Prior Publication Data

US 2008/0145324 A1    Jun. 19, 2008

Related U.S. Application Data

(63) Continuation of application No. PCT/EP2006/005333, filed on May 15, 2006.

(60) Provisional application No. 60/697,969, filed on Jul. 12, 2005.

(30) Foreign Application Priority Data

May 31, 2005    (FR) .................................... 05 51434

(51) Int. Cl.
   *A61K 8/00*    (2006.01)
(52) U.S. Cl.
   USPC .......................................................... 424/59

(58) Field of Classification Search
   CPC .................................. A61K 8/35; A61K 8/494
   See application file for complete search history.

(56) References Cited

U.S. PATENT DOCUMENTS

| | | | |
|---|---|---|---|
| 4,724,137 A | 2/1988 | Hoppe et al. | |
| 5,955,060 A | 9/1999 | Huglin et al. | |
| 6,018,044 A | 1/2000 | Huber | |
| 6,096,294 A * | 8/2000 | Hansenne et al. | 424/59 |
| 6,423,302 B1 | 7/2002 | Gers-Barlag et al. | |
| 6,514,485 B1 | 2/2003 | Malpede et al. | |
| 6,517,742 B1 * | 2/2003 | Richard et al. | 252/401 |
| 7,014,842 B2 * | 3/2006 | Dueva-Koganov et al. | 424/59 |
| 2005/0013784 A1 | 1/2005 | Trigg et al. | |

FOREIGN PATENT DOCUMENTS

| | | |
|---|---|---|
| EP | 0 517 104 A1 | 12/1992 |
| EP | 0 570 838 A1 | 11/1993 |
| EP | 0 775 698 A1 | 3/1997 |
| EP | 0 841 341 A1 | 5/1998 |
| EP | 0841341 A1 | 5/1998 |
| EP | 0933376 B1 | 8/1999 |
| EP | 1 034 778 A2 | 9/2000 |
| EP | 1 180 360 A2 | 2/2002 |
| EP | 1 582 201 A2 | 10/2005 |
| WO | WO 02/17873 A1 | 3/2002 |

* cited by examiner

*Primary Examiner* — David J Blanchard
*Assistant Examiner* — Tigabu Kassa
(74) *Attorney, Agent, or Firm* — Buchanan Ingersoll & Rooney, PC

(57) ABSTRACT

UV-photostable, topically applicable cosmetic/dermatological compositions contain at least one dibenzoylmethane UV-sunscreen compound and at least one photostabilizing silicon-containing s-triazine compound substituted with two aminobenzoate or aminobenzamide groups.

15 Claims, No Drawings

UV-PHOTOPROTECTIVE COMPOSITIONS COMPRISING DIEBENZOYLMETHANE SCREENING AGENTS AND SILICON-CONTAINING S-TRIAZINE COMPOUNDS SUBSTITUTED WITH TWO AMINOBENZOATE OR AMINOBENZAMIDE GROUPS

CROSS-REFERENCE TO PRIORITY/PCT/PROVISIONAL APPLICATIONS

This application claims priority under 35 U.S.C. §119 of FR 05/51434, filed May 31, 2005, and of Provisional Application No. 60/697,969, filed Jul. 12, 2005, and is a continuation of PCT/EP 2006/005333, filed May 15, 2006 and designating the United States, published in the English language as WO 2006/128732 A1 on Dec. 7, 2006, each hereby expressly incorporated by reference in its entirety and each assigned to the assignee hereof.

BACKGROUND OF THE INVENTION

1. Technical Field of the Invention

The present invention relates to photostabilizing at least one dibenzoylmethane compound against UV radiation by at least one silicon-containing s-triazine substituted with two aminobenzoate or aminobenzamide groups.

This invention also relates to novel compounds and compositions, in particular cosmetic/dermatological compositions for topical application containing a combination of a dibenzoylmethane compound and a silicon-containing s-triazine substituted with two aminobenzoate or aminobenzamide groups.

2. Description of Background and/or Related and/or Prior Art

Light radiation with wavelengths in the range 280 nm to 400 nm is known to brown the human epidermis; more particularly, rays with a wavelength in the range 280 to 320 nm, known as UV-B, are known to cause erythema and cutaneous burns which may be deleterious to the development of a natural tan. For those and for aesthetic reasons, there is a constant demand for means for controlling natural tanning which can thereby control the color of the skin; thus UV-B radiation must therefore be screened.

It is also known that UV-A rays with wavelengths in the range 320 to 400 nm, which cause the skin to brown, tend to induce an impairment therein, in particular with sensitive skin or skin which is continually exposed to solar radiation. In particular, UV-A radiation causes the skin to lose elasticity and the appearance of wrinkles, resulting in premature aging of the skin. The radiation promotes triggering of the erythematous reaction or amplifies that reaction in certain subjects and may even be the cause of phototoxic or photoallergic reactions. Hence, for aesthetic and cosmetic reasons, such as preserving the natural elasticity of the skin, for example, more and more individuals seek to control the effect of UV-A radiation on their skin. Thus, screening UV-A radiation is also desirable.

With the goal of ensuring protection of the skin and keratinous material against UV radiation, sunscreen compositions are generally used which comprise organic screens which are active in the UV-A and active in the UV-B regions. The majority of such screens are liposoluble.

In this respect, a current particularly advantageous family of UV-A screens is constituted by dibenzoylmethane compounds, in particular 4-tert-butyl-4'-methoxydibenzoyl methane, which have intrinsically good absorbing powers. Such dibenzoylmethane compounds, which are now well known per se as screens which are active in the UV-A region, have been described in FR-A-2,326,405 and FR-A-2,440,933, as well as in EP-A-0,114,607; 4-tert-butyl-4'-methoxydibenzoyl methane is currently marketed under the trademark "Parsol 1789" by ROCHE VITAMINS.

Unfortunately, it has been discovered that dibenzoylmethane compounds are relatively sensitive to ultraviolet radiation (in particular UV-A), i.e., more precisely, they have an annoying tendency to degrade at a greater or lesser rate under the action thereof. This substantial lack of photochemical stability of dibenzoylmethane compounds to the ultraviolet radiation to which they are by their very nature intended to be subjected cannot guarantee constant protection during prolonged exposure to the sun, and repeated applications at regular, close intervals have to be made by the consumer to effectively protect the skin against UV radiation.

1,3,5-Triazine derivatives are particularly desirable in solar cosmetics because they are strongly active in the UV-B region. They have in particular been described in U.S. Pat. No. 4,367,390, EP-A-0,863,145, EP-A-0,517,104, EP-A-0,570,838, EP-A-0,507,691, EP-A-0,796,851, EP-A-0,775,698, EP-A-0,878,469 and EP-A-0,933,376; the following in particular are known:

2,4,6-tris[p-(2'-ethylhexyl-1'-oxycarbonyl)anilino]-1,3,5-triazine, or "Ethylhexyl Triazone" (INCI name), marketed under the trademark "Uvinul T 150" by BASF;

2-[(p-(tertiobutylamido)anilino]-4,6-bis-[(p-(2'-ethylhexyl-1'-oxycarbonyl)anilino]-1,3,5-triazine or "Diethylhexyl Butamido Triazone" (INCI name), marketed under the trademark "UVASORB HEB" by SIGMA 3V. They have a strong UV-B absorbing power and it would thus be highly advantageous to be able to use them in combination with the 4-tert-butyl-4'-methoxydibenzoylmethane noted above to obtain products offering broad effective protection over the entire UV radiation range.

However, it has been shown that certain of these 1,3,5-triazine derivatives, when in the presence of 4-tert-butyl-4'-methoxydibenzoylmethane, are photosensitive, namely to UV radiation, and suffer from the disadvantage of undergoing major chemical degradation. Under such conditions, a combination of these two screens could no longer provide the skin and hair with prolonged broad-based protection against the sun.

SUMMARY OF THE INVENTION

It has now surprisingly been discovered that a particular family of silicon-containing s-triazine compounds substituted with two aminobenzoate or aminobenzamide groups, which are active in the UV-B region, on the one hand substantially improves the photochemical stability (or photostability) of dibenzoylmethane compounds. On the other hand, such particular s-triazine compounds are photostable even in the presence of a dibenzoylmethane compound.

These discoveries constitute the basis of the present invention.

Thus, the present invention features a method for improving the stability of at least one dibenzoylmethane compound against UV radiation, by combining with said dibenzoylmethane compound at least one s-triazine compound having formula (1) as defined below.

This invention also features compositions comprising at least one UV screening system, formulated into a physiologically acceptable support, which comprises:

(a) at least one UV screen of the dibenzoylmethane compound type; and (b) at least one s-triazine compound of formula (1) as defined below.

Finally, the present invention also features formulating an s-triazine compound of formula (1) into a composition comprising at least one dibenzoylmethane compound in a physiologically acceptable support to improve the stability of the dibenzoylmethane compound to UV radiation.

Other characteristics, aspects and advantages of the invention will become apparent from the following detailed description.

Herein, the term "system screening UV radiation" means an agent screening UV radiation constituted either by a single UV radiation-screening organic or mineral compound or a mixture of several UV radiation-screening organic or mineral compounds, for example a mixture comprising a UV-A screen and a UV-B screen.

The term "silicon-containing" means a compound comprising at least one diorganosiloxane group or a silane group in its structure.

DETAILED DESCRIPTION OF BEST MODE AND SPECIFIC/PREFERRED EMBODIMENTS OF THE INVENTION

Particularly exemplary dibenzoylmethane compounds according to the invention include:
2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane;
2,6-dimethyl-4-tert-butyl-4'-methoxydibenzoylmethane.

Of the dibenzoylmethane compounds indicated above, 4-isopropyl-dibenzoylmethane will in particular be used, marketed under the trademark "EUSOLEX 8020" by MERCK, having the following formula:

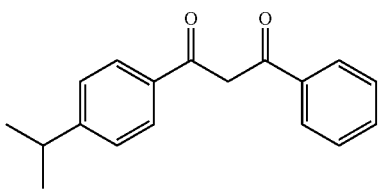 [SMILES: CC(C)c1ccc(C(=O)CC(=O)c2ccccc2)cc1]

More particularly, 4-(tert-butyl)-4'-methoxy dibenzoylmethane or Butyl Methoxy Dibenzoylmethane, marketed under the trademark "PARSOL 1789" by Roche Vitamins is preferably used; this screening agent has the following formula:

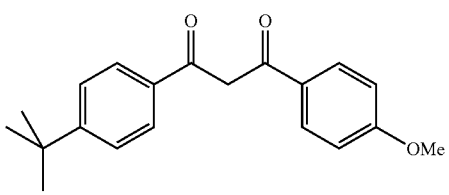 [SMILES: COc1ccc(C(=O)CC(=O)c2ccc(C(C)(C)C)cc2)cc1]

The dibenzoylmethane compound or compounds may be present in the compositions in accordance with the invention in amounts which preferably range from 0.01% to 20% by weight, more preferably 0.1% to 10% by weight, and even more preferably 0.1% to 6% by weight with respect to the total composition weight.

The compounds in accordance with the present invention have the following general formula (1) or one of its tautomeric forms:

in which:
the radicals R, which may be identical or different, are each a linear or branched $C_1$-$C_{30}$ alkyl radical, optionally halogenated or unsaturated, a $C_6$-$C_{12}$ aryl radical, a $C_1$-$C_{10}$ alkoxy radical or the trimethylsilyloxy group;
a=0 to 3;
the group D designates an s-triazine compound having the following formula (2):

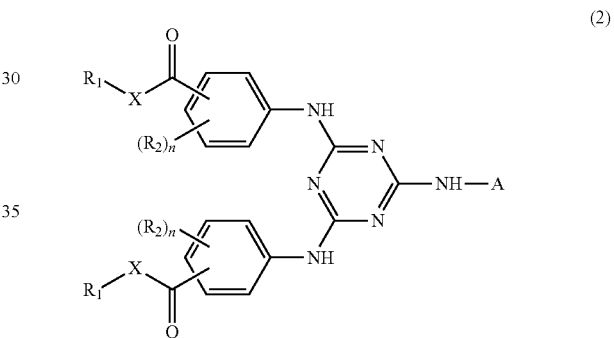

in which:
X is —O— or —NR$_3$—, in which R$_3$ is hydrogen or a $C_1$-$C_5$ alkyl radical;
R$_1$ is a linear or branched $C_1$-$C_{20}$ alkyl radical which is optionally unsaturated and optionally containing a silicon atom, a $C_5$-$C_{20}$ cycloalkyl radical, optionally substituted with 1 to 3 linear or branched $C_1$-$C_4$ alkyl radicals, the group —(CH$_2$CHR$_4$—O)$_m$R$_5$ or the group —CH$_2$—CH(OH)—CH$_2$—O—R$_6$;
R$_4$ is hydrogen or methyl; the group (C=O)XR$_1$ being in the position ortho-, meta- or para- to the amino group;
R$_5$ is hydrogen or a $C_1$-$C_8$ alkyl radical;
R$_6$ is hydrogen or a $C_4$-$C_8$ alkyl radical;
m is a whole number from 2 to 20;
n=0 to 2;
the radicals R$_2$, which may be identical or different, are each a hydroxyl radical, a linear or branched $C_1$-$C_8$ alkyl radical, a $C_1$-$C_8$ alkoxy radical; with the proviso that two R$_2$ radicals adjacent to the same aromatic ring may together form a dioxyalkylidene group in which the alkylidene group contains 1 or 2 carbon atoms;
A is a divalent radical selected from among methylene, —[CH(Si(CH$_3$)$_3$)]—, ethylene or a group having one of formulae (3), (4) or (5) below:

$$\text{---}(Z)\text{---}CH\text{---}CH_2\text{---} \quad (3)$$
$$\qquad\qquad\qquad |$$
$$\qquad\qquad\qquad W$$

$$\text{---}(Z)\text{---}CH=CH\text{---} \quad (4)$$

$$\qquad\qquad\quad CH_2 \quad (5)$$
$$\qquad\qquad\quad \|$$
$$\text{---}(Z)\text{---}C\text{---}$$

in which:

Z is a linear or branched, saturated or unsaturated $C_1$-$C_{10}$ alkylene diradical, optionally substituted with a hydroxyl radical or oxygen and optionally containing an amino group;

W is a hydrogen atom, a hydroxyl radical or a linear or branched, saturated or unsaturated $C_1$-$C_8$ alkyl radical.

It should be noted that the compounds of formula (1) may be used in their tautomeric forms and more particularly in the following tautomeric form with formula (1') below:

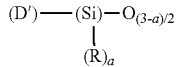

in which the group D' is an s-triazine compound having the following formula (2'):

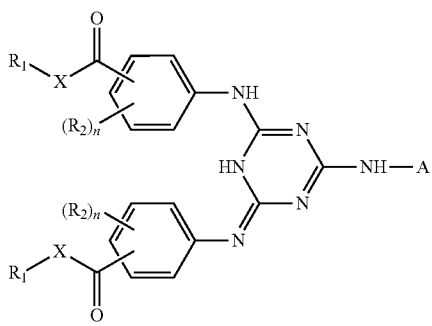

In addition to units of formula -A-(Si)(R)$_a$(O)$_{(3-a)/2}$, the organosiloxane may comprise structural units with formula

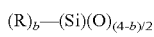

in which:

R has the same definition as in formula (1);

b=1, 2 or 3.

In formulae (2) and (2') as defined above, the alkyl radicals may be linear or branched, saturated or unsaturated and selected in particular from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. Particularly preferably, the alkyl radical is the methyl radical.

Preferred s-triazine derivatives are those which have at least one, more preferably all of the following characteristics in formula (2) or (2'):

R and $R_1$ are methyl;

a=2;

X is O;

$R_1$ is a $C_4$-$C_5$ radical;

$R_2$ and $R_3$ are hydrogen;

$R_4$ is H or OH;

The group (C=O)$XR_1$ is in the position para- to the amino group;

A is the propyl radical.

Preferably, the s-triazine compounds of the invention have the formulae (1a), (1b) or (1c) below:

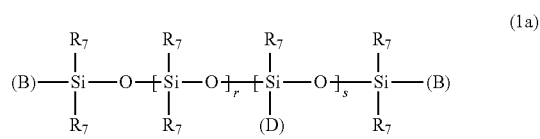

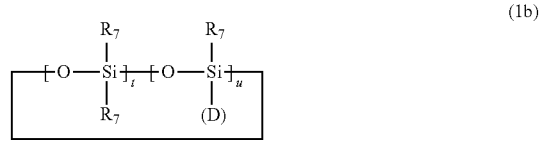

in which:

(D) has formula (2) as defined above;

the radicals $R_7$, which may be identical or different, are each selected from among linear or branched $C_1$-$C_{20}$ alkyl radicals, phenyl, 3,3,3-trifluoropropyl and trimethylsilyloxy, at least 80% by number of the $R_7$ radicals being methyl;

the radicals $R_8$, which may be identical or different, are each selected from among linear or branched $C_1$-$C_{20}$ alkyl and alkenyl or phenyl radicals;

the radicals (B), which may be identical or different, are each selected from among $R_7$ radicals and the radical (D);

r is a whole number ranging from 0 to 200 inclusive;

s is a whole number ranging from 0 to 50 and if s=0, at least one of the two symbols (B) designates (D);

u is a whole number ranging from 1 to 10;

t is a whole number ranging from 0 to 10, with the proviso that t+u equals 3 or more, and tautomeric forms thereof.

Linear diorganosiloxanes of formula (1a) are particularly preferred.

Linear or cyclic diorganosiloxanes of formula (1a) or (1b) according to the present invention are random oligomers or polymers preferably having at least one, and more preferably all of the following characteristics:

$R_7$ is alkyl; more preferably, it is methyl;

B is preferably methyl (case of linear compounds of formula (1a)).

Particularly preferred examples of compounds having formula (1) are the following compounds with formulae (a) to (i) and tautomeric forms thereof:

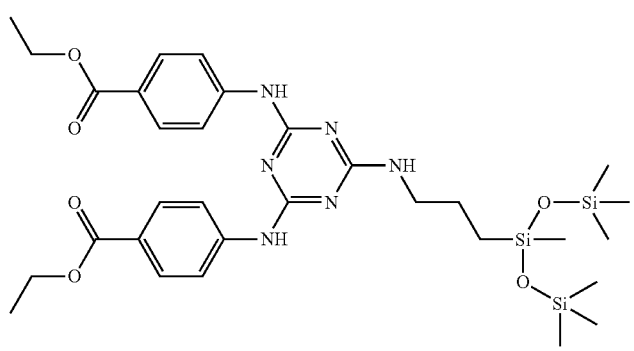
(a)
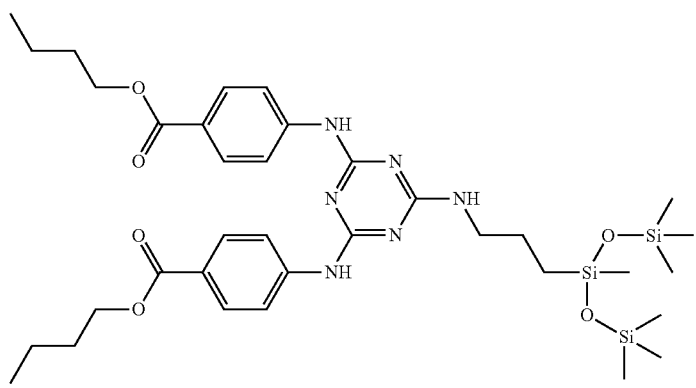
(b)
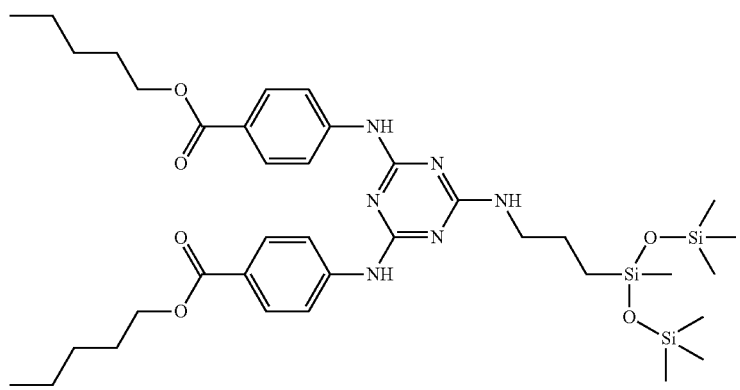
(c)
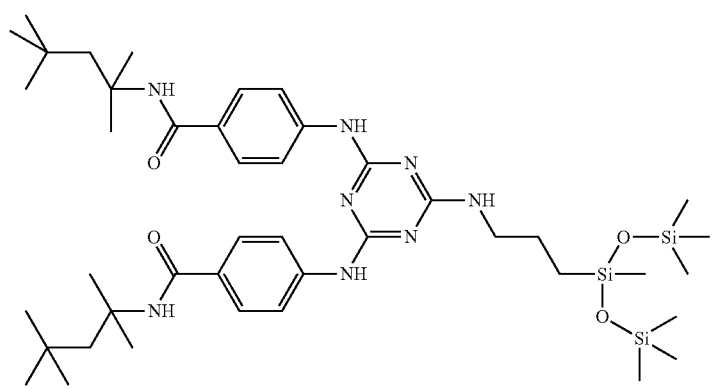
(d)

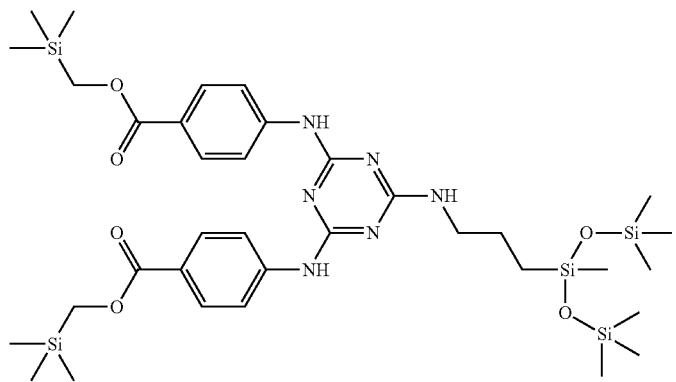
(e)
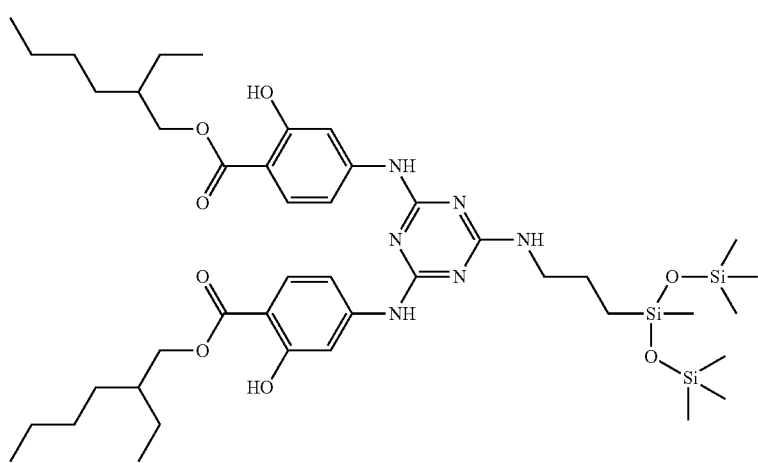
(f)
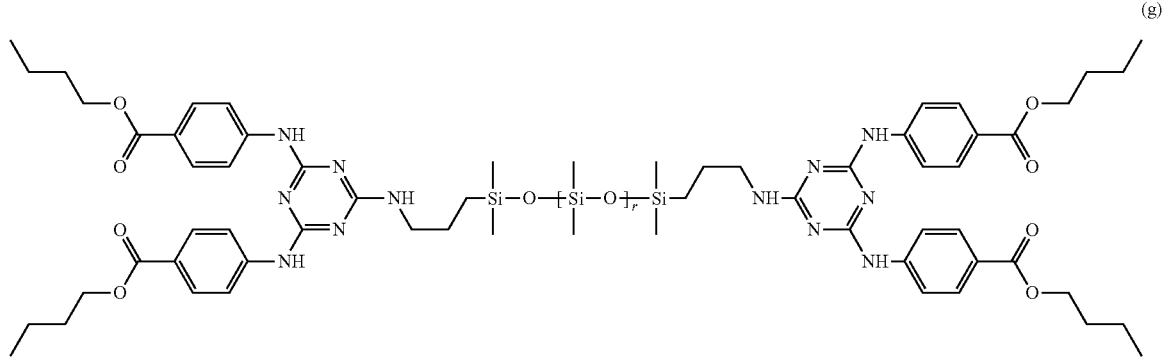
(g)
in which r=8.1

(h)

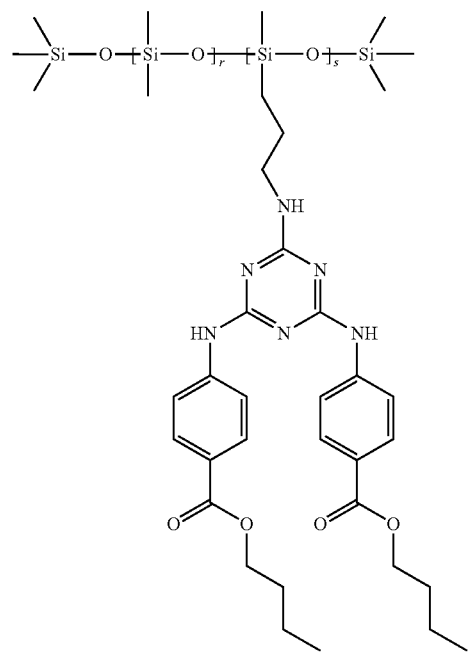

A first family of novel compounds having formula (1) is constituted by those in which in formula (2), the radical X is $NR_3$ in which $R_3$ has the same meaning as indicated above, and tautomeric forms thereof. An example of a compound having said structure is 2,4-bis[(1,1,3,3-tetramethylbutyl) 4'-diylaminobenzamide]-6-{[1,3,3,3-tetramethyl-1-[(trimethylsilyl)oxy]disiloxanyl]propyl-3-ylamino}-s-triazine of formula (d) below:

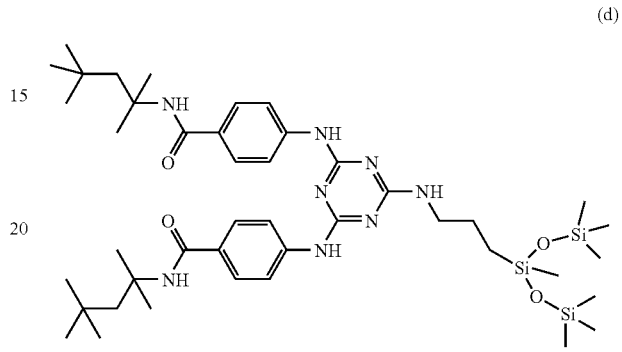

(d)

(i)

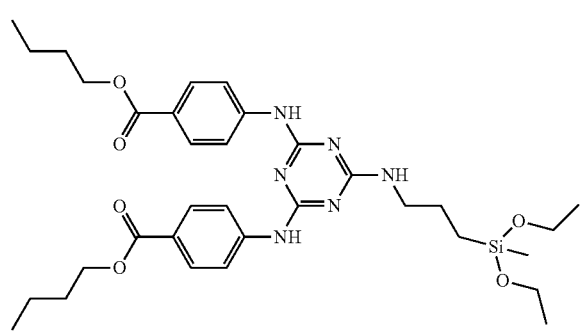

A second family of novel compounds of formula (1) is constituted by those in which, in formula (2), the radical X is O and at least one of the groups $(C=O)XR_1$ is in the position ortho- to the amino group, and preferably the two groups $(C=O)XR_1$ are in the position ortho- to the amino group, and tautomeric forms thereof.

A third family of novel compounds of formula (1) is constituted by those having the following formula (1c):

$$(D)\text{-Si}(R_8)_3 \qquad (1c)$$

in which $R_8$ has the meaning indicated above, and tautomeric forms thereof.

Novel compounds of formula (1) which may also be cited include:

More particularly, the following compound having structure (b) is employed: 2,4-bis(n-butyl 4'-diylaminobenzoate)-6-{[1,3,3,3-tetramethyl-1-[(trimethylsilyl)oxy]disiloxanyl] propyl-3-ylamino}-s-triazine:

2,4-bis(methyltrimethylsilyl-4'-diylaminobenzoate)-6-{[1,3,3,3-tetramethyl-1-[(trimethylsilyl)oxy]disiloxanyl]propyl-3-ylamino}-s-triazine with structure (e):

(b)

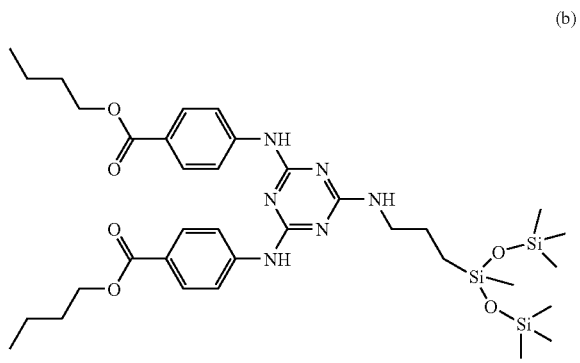 [SMILES: CCCCOC(=O)c1ccc(Nc2nc(NCCC[Si](C)(O[Si](C)(C)C)O[Si](C)(C)C)nc(Nc3ccc(C(=O)OCCCC)cc3)n2)cc1]

(e)

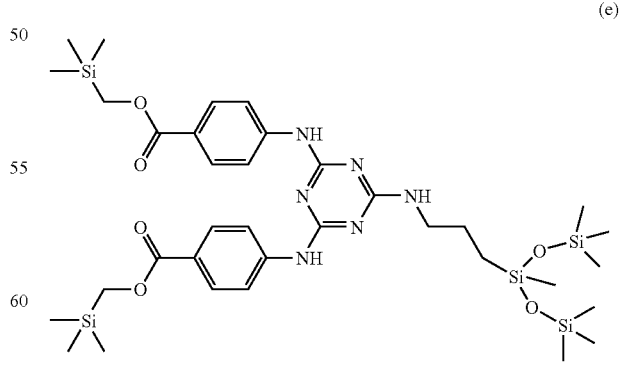

Certain compounds of formula (1) and their tautomeric forms are known and have been described in EP-A-0,841,341 and others are novel and constitute another aspect of the invention.

2,4-bis(2-ethylhexyl 2'-hydroxy-4'-diylaminobenzoate)-6-{[1,3,3,3-tetramethyl-1-[(trimethylsilyl)oxy]disiloxanyl] propyl-3-ylamino}-s-triazine with structure (f):

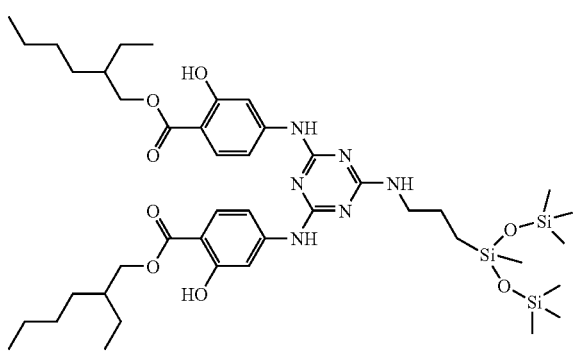

the random derivative having the following formula (g):

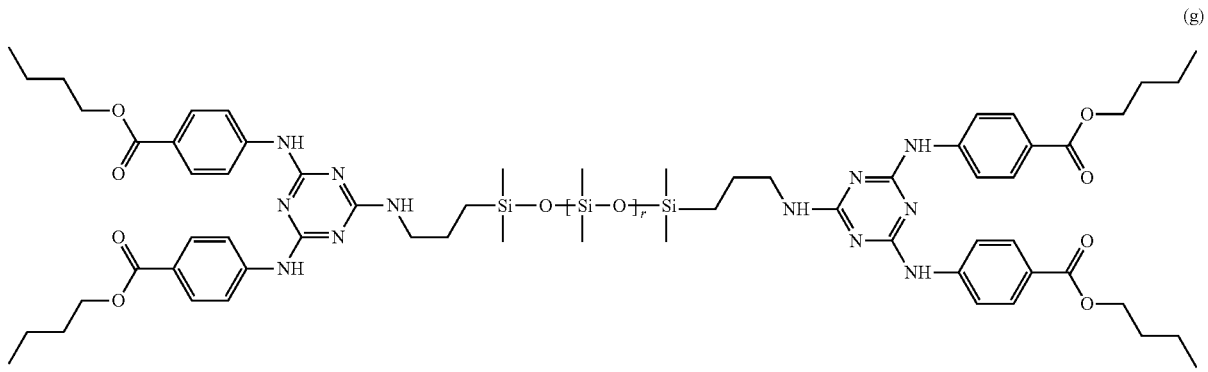

in which r=8.1.

The compounds of formula (1) may be prepared in accordance with the following reaction scheme:

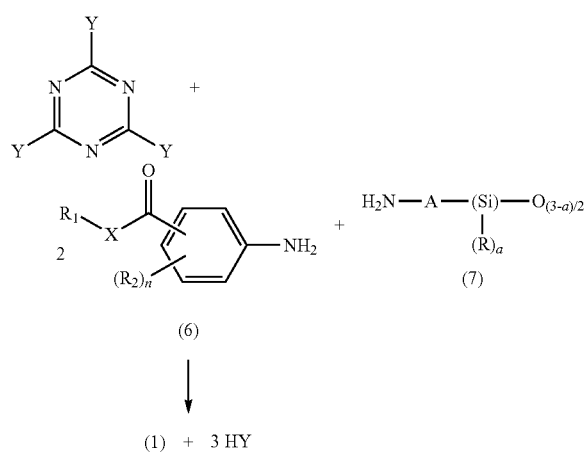

in which R, $R_1$, $R_2$, A, n and a are as defined above and Y is a halogen, in particular chlorine or bromine.

The reagents may be introduced in any order; 2 equivalents of derivative with formula (6) followed by one equivalent of derivative with formula (7) (pathway I) or 1 equivalent of derivative with formula (7) followed by 2 equivalents of derivative with formula (6) (pathway II).

The above reactions may optionally be carried out in the presence of a solvent (for example: THF, acetone/water for the first step; toluene, xylene or 1,2-dichloroethane for the second step), at a temperature in the range 0° C. to 200° C., more particularly 0° C. to 20° C. for the first step and 50° C. to 120° C. for the second step and in the presence or absence of a base to capture the acid formed (for example sodium bicarbonate, sodium carbonate, aqueous sodium hydroxide, triethylamine or pyridine). They may also be carried out in a microwave oven in the presence or absence of a solvent (for example: toluene, xylene or 1,2-dichloroethane) or in the presence or absence of 10% of graphite, at a temperature of 50° C. to 150° C., at a power of 50-150 watts for a period of 10 to 30 minutes.

When a is equal to 1-3 and R is an alkoxy, polymerization of monomeric alkoxysilane derivatives may be carried out using conventional silicone chemistry methods.

The preparation of amino derivatives of benzoic acid with formula (6) has been described, in particular, in FR-A-2,151, 503. Particularly suitable amino derivatives of benzoic acid for preparing the compounds according to the invention which are exemplary are butyl 4-amino benzoate and pentyl-4-aminobenzoate.

Aminated silicones having formula (7) may be obtained from Dow Corning Toray Silicone Co Ltd, such as those with an α,ω-diamino structure such as BY16-853 (viscosity: 30; $NH_2$ equivalent: 650) or BY16-853B (viscosity: 80; $NH_2$ equivalent: 2200) or those with pendent group structures, such as BY16-828 (viscosity: 120; $NH_2$ equivalent: 3500) or BY16-850 (viscosity: 1100; $NH_2$ equivalent: 4000).

The aminomethyltrimethylsilane marketed by Gelest is bis (trimethylsilyl)methylamine (RN 134340-00-4).

Triazine derivatives having formula (1) in accordance with the invention are preferably present in the subject compositions in amounts of 0.01% to 20% by weight, more preferably 0.1% to 10%, more preferably 0.1% to 6% by weight with respect to the total composition weight.

According to the present invention, the triazine derivative or derivatives with formula (1) will be used in a quantity sufficient to obtain a substantial and significant improvement in the photostability of the dibenzoylmethane compound in a given composition. This minimum quantity of photostabilizing agent to be used may vary depending on the starting quantity of dibenzoylmethane present in the composition and depending on the nature of the cosmetically acceptable support used in the composition. It may be determined without difficulty using a conventional photostability measuring test.

The compositions according to the invention are generally suited for topical application to the skin and thus generally comprise a physiologically acceptable medium, i.e., compatible with the skin and/or integuments (hair, eyelashes, eyebrows, nails). Preferably, it is a cosmetically acceptable medium, i.e., with an agreeable color, odor and feel which does not generate unacceptable discomfort (smarting, tightness, redness), which may deter the consumer from using that composition.

The compositions in accordance with the invention will preferably comprise other complementary organic or inorganic photoprotective agents which are active in the UV-A and/or UV-B region, which are hydrophilic or lipophilic or even insoluble in the cosmetic solvents in routine use.

The complementary organic photoprotective agents are selected in particular from among anthranilates; cinnamic derivatives; salicylic derivatives; camphor derivatives; benzophenone derivatives; β,β-diphenylacrylate derivatives; benzotriazole derivatives; benzalmalonate derivatives; benzimidazole derivatives; imidazolines; bis-benzoazolyl derivatives such as those described in EP-A-0,669,323 and U.S. Pat. No. 2,463,264; p-aminobenzoic acid (PABA) derivatives; methylene bis(hydroxyphenyl benzotriazole) derivatives as described in U.S. Pat. Nos. 5,237,071, 5,166,355, GB-2303549, DE-A-19726184 and in EP-A-0,893,119; polymeric screens and silicone screens such as those described in WO-A-93/04665; dimeric α-alkylstyrene derivatives such as those described in DE-19855649; 4,4-diarylbutadienes as described in EP-A-0,096,720, DE-19746654, DE-19755649, EP-A-1,008,586, EP-A-1,133,980 and EP-A-0,133,981 and mixtures thereof.

Examples of complementary organic photoprotective agents which are exemplary are those designated below under their INCI names:

Para-Aminobenzoic Acid Derivatives

PABA;
Ethyl PABA;
Ethyl Dihydroxypropyl PABA;
Ethylhexyl Dimethyl PABA, marketed in particular under the trademark "ESCALOL 507" by ISP;
Glyceryl PABA;
PEG-25 PABA, marketed under the trademark "UVINUL P25" by BASF;

Salicylic Derivatives

Homosalate, marketed under the trademark "Eusolex HMS" by Rona/EM Industries;
Ethylhexyl Salicylate, marketed under the trademark "NEO HELIOPAN OS" by HAARMANN and REIMER;
Dipropyleneglycol Salicylate, marketed under the trademark "DIPSAL" by SCHER;
TEA Salicylate, marketed under the trademark "NEO HELIOPAN TS" by HAARMANN and REIMER;

Cinnamic Derivatives

Ethylhexyl Methoxycinnamate, marketed in particular under the trademark "PARSOL MCX" by HOFFMANN LA ROCHE;
Isopropyl Methoxy cinnamate;
Isoamyl Methoxy cinnamate, marketed under the trademark "NEO HELIOPAN E 1000" by HAARMANN and REIMER;
Cinoxate;
DEA Methoxycinnamate;
Diisopropyl Methylcinnamate;
Glyceryl Ethylhexanoate dimethoxycinnamate;

β,β-Diphenylacrylate Derivatives

Octocrylene, marketed in particular under the trademark "UVINUL N539" by BASF;
Etocrylene, marketed in particular under the trademark "UVINUL N35" by BASF;

Benzophenone Derivatives

Benzophenone-1, marketed under the trademark "UVINUL 400" by BASF;
Benzophenone-2, marketed under the trademark "UVINUL D50" by BASF;
Benzophenone-3 or Oxybenzone, marketed under the trademark "UVINUL M40" by BASF;
Benzophenone-4, marketed under the trademark "UVINUL MS40" by BASF;
Benzophenone-5;
Benzophenone-6, marketed under the trademark "Helisorb 11" by Norquay;
Benzophenone-8, marketed under the trademark "Spectra-Sorb UV-24" by American Cyanamid;
Benzophenone-9, marketed under the trademark "UVINUL DS-49" by BASF;
Benzophenone-12;
n-Hexyl 2-(4-diethylamino-2-hydroxybenzoyl)benzoate, marketed under the trademark "UVINUL A+" by BASF;

Benzylidene Camphor Derivatives 3-benzylidene camphor manufactured under the trademark "MEXORYL SD" by CHIMEX;
4-methyl benzylidene camphor, marketed under the trademark "EUSOLEX 6300" by MERCK;
Benzylidene Camphor Sulfonic Acid, manufactured under the trademark "MEXORYL SL" by CHIMEX;
Camphor Benzalkonium Methosulfate, manufactured under the trademark "MEXORYL SO" by CHIMEX;
Terephthalylidene Dicamphor Sulfonic Acid, manufactured under the trademark "MEXORYL SX" by CHIMEX;
Polyacrylamidomethyl Benzylidene Camphor, manufactured under the trademark "MEXORYL SW" by CHIMEX;

Phenyl Benzimidazole Derivatives

Phenylbenzimidazole Sulfonic Acid, marketed under the trademark "EUSOLEX 232" by MERCK;
Disodium Phenyl Dibenzimidazole Tetra-sulfonate, marketed under the trademark "NEO HELIOPAN AP" by HAARMANN and REIMER;

Phenyl Benzotriazole Derivatives

Drometrizole Trisiloxane, marketed under the trademark "Silatrizole" by RHODIA CHIMIE;
Methylene bis-Benzotriazolyl Tetramethylbutylphenol, marketed in the solid form under the trademark "MIXXIM BB/100" by FAIRMOUNT CHEMICAL or in the micronized form in aqueous dispersion under the trademark "TINOSORB M" by CIBA SPECIALTY CHEMICALS;

Anthranilic Derivatives

Menthyl anthranilate, marketed under the trademark "NEO HELIOPAN MA" by HAARMANN and REIMER;

Imidazoline Derivatives

Ethylhexyl Dimethoxybenzylidene Dioxoimidazoline Propionate;

Benzalmalonate Derivatives

Di-neopentyl 4'-methoxybenzalmalonate;
Polyorganosiloxane with benzalmalonate functions, such as Polysilicone-15, marketed under the trademark "PARSOL SLX" by HOFFMANN LA ROCHE;

4,4-Diarylbutadiene Derivatives 1,1-dicarboxy(2,2'-dimethylpropyl)-4,4-diphenylbutadiene;

Benzoxazole Derivatives 2,4-bis-[5-1 (dimethylpropyl)benzoxazol-2-yl-(4-phenyl)-imino]-6-(2-ethylhexyl)-imino-1,3,5-triazine, marketed under the trademark "Uvasorb K2A" by Sigma 3V;
and mixtures thereof.

Preferred complementary organic photoprotective agents are selected from among:
Ethylhexyl Methoxycinnamate;
Homosalate;
Ethylhexyl Salicylate;
Butyl Methoxydibenzoylmethane;
Octocrylene;
Phenylbenzimidazole Sulfonic Acid;
Benzophenone-3;
Benzophenone-4;
Benzophenone-5;
n-Hexyl 2-(4-diethylamino-2-hydroxybenzoyl)-benzoate;
4-Methylbenzylidene camphor;
Terephthalylidene Dicamphor Sulfonic Acid;
Disodium Phenyl Dibenzimidazole Tetra-sulfonate;
Methylene bis-Benzotriazolyl Tetramethylbutylphenol;
Drometrizole Trisiloxane;
Polysilicone-15;
Di-neopentyl 4'-methoxybenzalmalonate;
1,1-Dicarboxy(2,2'-dimethylpropyl)-4,4-diphenylbutadiene;
and mixtures thereof.

The inorganic photoprotective agents are selected from among pigments or nanopigments (mean primary particle size: generally from 5 nm and 100 nm, preferably from 10 nm and 50 nm) of metallic oxides which may or may not be coated, for example titanium oxide nanopigments (amorphous or crystalline in the rutile and/or anatase form), iron, zinc, zirconium or cerium, and mixtures thereof. Conventional coating agents include alumina and/or aluminum stearate. Such metallic oxide nanopigments, which may or may not be coated, are in particular described in EP-A-0,518,772 and EP-A-0,518,773.

The additional photoprotective agents are generally present in the compositions according to the invention in proportions of 0.01% to 20% by weight with respect to the total composition weight, preferably 0.1% to 10% by weight with respect to the total composition weight.

The compositions of the invention may be in any of the forms which are suitable for topical application, in particular in the form of aqueous gels, in the form of emulsions obtained by dispersion of a fat phase (also termed the oily phase) in an aqueous phase (O/W) or the reverse (W/H), or multiple emulsions (for example W/O/E or O/W/O or O/O/W). They may be more or less fluid and have the appearance of a white or colored cream, a pomade, a milk, a lotion, a serum, a paste, a powder, a solid stick, and may optionally be packaged as an aerosol and in the form of a foam or spray. These compositions are prepared using the usual methods.

In a particular embodiment of the invention, the composition is in the form of an emulsion and then comprises at least one oily phase. The proportion of the oily phase of the emulsion may be from 1% to 80% by weight, preferably 2% to 50% by weight and more preferably 2% to 40% by weight with respect to the total composition weight. The fats in the oily phase, in particular oils, and the emulsifying and co-emulsifying agents which may be present, used in the composition in the form of an emulsion are selected from those conventionally used in the cosmetics or dermatological field. The emulsifying and co-emulsifying agent, when present, are generally present in a proportion of 0.1% to 30% by weight, preferably 0.3% to 20% by weight and more preferably 0.5% to 15% by weight with respect to the total composition weight. The emulsion may also contain lipid vesicles in addition to or in place of the emulsifying and/or co-emulsifying agents.

The emulsions generally contain at least one emulsifying agent selected from amphoteric, anionic, cationic or nonionic emulsifying agents used alone or as a mixture. The emulsifying agents are suitably selected as a function of the continuous phase of the emulsion to be produced (W/H or O/W). When the emulsion is a multiple emulsion, it generally comprises an emulsifying agent in the primary emulsion and an emulsifying agent in the external phase into which the primary emulsion is introduced.

Emulsifying agents which may be used to prepare W/H emulsions which may be cited, are for example alkyl esters or sorbitan ethers, glycerol or sugars; silicone surfactants such as dimethicone copolyols, such as the mixture of cyclomethicone and dimethicone copolyol, marketed under the trademarks DC 5225 C and DC 3225 C by Dow Corning and such as alkyl-dimethicone copolyols such as Laurylmethicone copolyol marketed under the trademark "Dow Corning 5200 Formulation Aid" by Dow Corning, Cetyl dimethicone copolyol marketed under the trademark Abil EM 90® by Goldschmidt and the mixture of Polyglyceryl-4 isostearate/Cetyl dimethicone copolyol/Hexyl laurate marketed under the trademark Abil WE 09® by Goldschmidt. It is also possible to add thereto one or more co-emulsifying agents which, advantageously, may be selected from the group comprising esters of fatty acids with a branched chain and polyol, in particular esters of fatty acid with a branched chain and glycerol and/or sorbitan and, for example, polyglyceryl isostearate, such as the product marketed under the trademark Isolan GI 34 by Goldschmidt, sorbitan isostearate, such as the product marketed under the trademark Arlacel 987 by ICI, sorbitan isostearate and glycerol, such as the product marketed under the trademark Arlacel 986 by ICI, and mixtures thereof.

Examples of emulsifying agents suitable for the preparation of O/W emulsions which are exemplary are nonionic emulsifying agents such as esters of fatty acids and oxyalkylenated polyols (more particularly polyoxyethylenated), for example polyethylene glycol stearates such as PEG-100 stearate, PEG-50 stearate and PEG-40 stearate; esters of fatty acids and oxyalkylenated sorbitan comprising 20 to 1000 E, for example, and for example those marketed under the trademark Tween 20 or Tween 60 by Uniqema; ethers of oxyalkylenated (oxyethylenated and/or oxypropylenated) fatty alcohols; esters of sugars, alkoxylated or not, such as sucrose stearate and such as PEG-20 methylglucose sesquistearate; sorbitan esters such as sorbitan palmitate marketed under the trademark Span 40 by Uniqema; esters of a dibasic acid and a fatty alcohol, such as dimyristyl tartrate; mixtures of these emulsifying agents such as a mixture of glyceryl stearate and PEG-100 stearate (CTFA name: Glyceryl Stearate/PEG-100 Stearate) marketed under the trademark Arlacel 165 by Uniqema and under the trademark SIMULSOL 165 by SEPPIC; or the mixture of dimyristyl tartrate, cetearyl alcohol, Pareth-7 and PEG-25 laureth-25, marketed under the trademark Cosmacol PSE by Sasol (CTFA name: Dimyristyl tartrate/cetearyl alcohol/12-15 Pareth 7/PPG 25 laureth 25).

Co-emulsifying agents may be added to said emulsifying agents, such as fatty alcohols containing 8 to 26 carbon atoms, such as cetyl alcohol, stearyl alcohol and a mixture thereof (cetearyl alcohol), octyldodecanol, 2-butyloctanol, 2-hexyldecanol, 2-undecylpentadecanol or oleic alcohol, or fatty acids, for example.

It is also possible to prepare emulsions without emulsifying surfactants or containing less than 0.5% of the total composition weight, using suitable compounds which can stabilize said emulsions, for example amphiphilic polymers, electrolytes.

When the compositions of the invention are in the form of an emulsion, these comprise at least one oily phase which contains at least one oil, in particular a cosmetic oil. The term "oil" means a fat which is liquid at ambient temperature (25° C.).

Examples of oils which can be used in the compositions of the invention are hydrocarbon-containing oils of animal origin such as perhydrosqualene (or squalane); hydrocarbon-containing oils of vegetable origin, such as caprylic/capric acid triglycerides such as those marketed by Stearineries Dubois or those marketed under the trademark Miglyol 810, 812 and 818 by Dynamit Nobel, or oils of vegetable origin, for example sunflower, corn, soya, gourd, grapeseed, sesame, hazelnut, apricot, macadamia nut, arara, coriander, castor, avocado, jojoba oil, shea butter oil; synthesized oils; silicone oils such as volatile or non-volatile polymethylsiloxanes (PDMS) with a linear or cyclic silicone chain, which are liquid or pasty at ambient temperature; fluorinated oils such as partially hydrocarbonated and/or silicone oils, such as those described in Japanese JP-A-2-295912; ethers such as dicapryl ether (CTFA name: Dicaprylyl ether); and benzoates of $C_{12}$-$C_{15}$ fatty alcohols (Finsolv TN from FINETEX); arylalkyl benzoate derivatives such as 2-phenylethyl benzoate (X-Tend 226 from ISP); amide oils such as isopropyl N-lauroylsarcosinate (ELDEW SL-205 from Ajimoto) and mixtures thereof.

The oily phase may also comprise one or more fats selected, for example, from among fatty alcohols (cetyl alcohol, stearyl alcohol, cetearyl alcohol), fatty acids (stearic acid) and waxes (paraffin, polyethylene waxes, carnauba, beeswax).

The compositions of the invention may also contain one or more organic solvents which may be selected from the group constituted by hydrophilic organic solvents, lipophilic organic solvents, amphiphilic solvents or mixtures thereof.

Examples of hydrophilic organic solvents which may be cited, for example, are linear or branched monohydric alcohols containing 1 to 8 carbon atoms, such as ethanol, propanol, butanol, isopropanol or isobutanol; polyethylene glycols containing 6 to 80 ethylene oxides; polyols such as propylene glycol, isoprene glycol, butylene glycol, glycerol or sorbitol; mono- or di-alkyl isosorbides the alkyl groups of which contain 1 to 5 carbon atoms, such as dimethyl isosorbide; glycol ethers such as diethylene glycol mono-methyl or mono-ethyl ether and propylene glycol ethers such as dipropylene glycol methyl ether.

Amphiphilic organic solvents which may be cited include polypropylene glycol (PPG) derivatives, such as esters of polypropylene glycol and fatty acids, PPG and fatty alcohol such as PPG-23 oleyl ether and PPG-36 oleate.

Examples of lipophilic organic solvents which may be cited are fatty esters such as diisopropyl adipate, dioctyl adipate or alkyl benzoates.

The compositions of the present invention may also comprise conventional cosmetic adjuvants selected from softeners, moisturizers, opacifying agents, stabilizers, emollients, silicones, anti-foaming agents, fragrances, preservatives, anionic, cationic, nonionic, zwitterionic or amphoteric surfactants, fillers, polymers, propellants, alkalinizing or acidifying agents or any other ingredient which is normally used in the cosmetics and/or dermatological field.

Hydrophilic thickeners which may be cited include carboxyvinyl polymers such as carbopols (carbomers) and Pemulens (Copolymer acrylate/C10-C30-alkylacrylate); cellulose derivatives such as hydroxyethylcellulose; polysaccharides and in particular, gums such as xanthan gum; and mixtures thereof.

Lipophilic thickeners which may be cited include modified clays, such as hectorite and its derivatives, for example products marketed under the trademark Bentone.

Preservatives which are exemplary include parahydroxybenzoic acid esters also known as Parabens® (in particular methyl paraben, ethyl paraben, propyl paraben), phenoxyethanol, formol liberators such as, for example, imidazolidinyl urea or diazolidinyl urea, chlorhexidine digluconate, sodium benzoate, caprylyl glycol, iodopropynyl butyl carbamate, pentylene glycol, alkyl trimethylammonium bromide such as myristyl-trimethylammonium bromide (CTFA name: Myrtrimonium bromide), dodecyl-trimethylammonium bromide, hexadecyltrimethylammonium bromide, and mixtures thereof such as the mixture marketed under the trademark Cetrimide® by FEF CHEMICALS. The preservative may be present in the composition of the invention in an amount of 0.001% to 10% by weight with respect to the total composition weight, especially 0.1% to 5% by weight, and in particular 0.2% to 3% by weight.

Examples of fillers which may be used in the compositions of the invention which may be cited are, for example, pigments; silica powder; talc; polyamide particles, in particular those marketed under the trademark ORGASOL by Atochem; polyethylene powders; powders of natural organic materials such as starch powders, in particular of corn, wheat or rice starch, which may or may not be cross-linked, such as powders of starch cross-linked by octenylsuccinate anhydride, marketed under the trademark DRY-FLO by National Starch; microspheres based on acrylic copolymers, such as those formed from an ethylene glycol dimethacrylate/lauryl methacrylate copolymer marketed by Dow Corning under the trademark POLYTRAP; polymethylmethacrylate powders such as those marketed under the trademark MICROPEARL M 100 by Matsumoto; expanded powders such as hollow microspheres, in particular microspheres marketed under the trademark EXPANCEL by Kemanord Plast or under the trademark MICROPEARL F 80 ED by Matsumoto; silicone resin microbeads, such as those marketed under the trademark TOSPEARL by Toshiba Silicone; polyurethane powders, such as hexamethylene diisocyanate/trimethylol hexyllactone copolymer marketed under the trademark Plastic Powder D-400 by Toshiba Pigment (CTFA name: HDI/Trimethylol Hexyllactone Crosspolymer); and mixtures thereof. When they are present, these fillers may be in quantities of 0.001% to 20% by weight, preferably 0.1% to 10% by weight and more preferably 1% to 5% by weight with respect to the total composition weight.

Clearly, one skilled in the art will take care to select any complementary compounds as cited above and/or their quantities such that the advantageous properties intrinsically attached to the combination in accordance with the invention are not impaired or not substantially impaired by the envisaged adjuncts.

The compositions of the invention may constitute a skin care product, in particular for the face, the neck, the contours of the eye, the body; or a skin makeup product such as a tinting product (in particular a foundation), an eye shadow, a blusher, an eye-liner, a concealer, a body makeup product, a sun protection product or a skin cleansing product. Preferably, the compositions of the invention are sun protection products.

The composition is generally not washed off, but may be washed off if it constitutes a cleansing product, in particular a foaming product.

The invention also provides a method, whether regime or regimen, for the cosmetic/dermatological treatment of a keratinous material such as the skin, hair, eyelashes, eyebrows, lips, nails or mucosal membranes, wherein a composition as defined above is applied to the keratinous material.

The compositions of the invention may be in the form of sprayable fluid lotions in accordance with the invention which are applied to the skin or the hair in the form of fine particles using pressurization devices. The devices of the invention are well known to one skilled in the art and include non-aerosol pumps or atomizers, aerosol receptacles comprising a propellant and aerosol pumps using compressed air as the propellant. These latter have been described in U.S. Pat. Nos. 4,077,441 and 4,850,517.

Compositions packaged in aerosol form in accordance with the invention generally contain conventional propellants such as hydrofluorinated compounds, dichlorodifluoromethane, difluoroethane, dimethylether, isobutane, n-butane, propane or trichlorofluoromethane. They are preferably present in quantities of 15% to 50% by weight with respect to the total composition weight.

In order to further illustrate the present invention and the advantages thereof, the following specific examples are given, it being understood that same are intended only as illustrative and in nowise limitative. In said examples to follow, all parts and percentages are given by weight, unless otherwise indicated.

SYNTHESIS EXAMPLES

Example 1

Preparation of 2,4-bis(ethyl 4'-diylaminobenzoate)-6-{[1,3,3,3-tetramethyl-1-[(trimethylsilyl)oxy]disiloxanyl]propyl-3-ylamino}-s-triazine

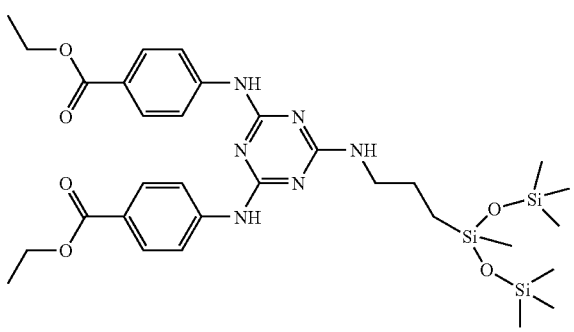

(a)

First Step

Preparation of 2,4-dichloro-6-{[1,3,3,3-tetramethyl-1-[(trimethylsilyl)oxy]disiloxanyl]propyl-3-ylamino}-s-triazine 1-amino-[1,3,3,3-tetramethyl-1-[(trimethylsilyl)oxy]disiloxanyl]-3-propane (41.7 g, 0.149 mol) and a solution of sodium bicarbonate (11.4 g, 0.135 mol) in 120 ml of water were added dropwise at 0° C. to a solution of cyanuryl chloride (25 g, 0.135 mol) in 250 ml of acetone so that the pH was from 3 and 6.5. Following introduction, the pH was 6.5. Stirring was then maintained for 1 hour 30 minutes at 10° C., then left at laboratory temperature. The precipitate formed was filtered, washed with water, drained and dried. 55.2 g (yield: 95%) of the expected derivative were obtained in the form of a white powder (MP: 59° C.).

Second Step

Preparation of Derivative of Example 1

A mixture of the above product (2.1 g, 0.005 mol) and ethyl para-aminobenzoate (1.65 g, 0.01 mol) in suspension in 20 ml of toluene was heated under reflux for 1 hour 30 minutes. It was cooled and hot heptane was added to the resin obtained. After grinding, filtering and drying, 2.3 g (yield: 67%) of the derivative of Example 1 were obtained in the form of a white powder:
MP: 106-108° C.
UV (ethanol): $\lambda_{max}$=311 nm; E1%=1147.

Example 2

Preparation of 2,4-bis(n-butyl-4'-diylaminobenzoate)-6-{[1,3,3,3-tetramethyl-1-[(trimethylsilyl)oxy]disiloxanyl]propyl-3-ylamino}-s-triazine

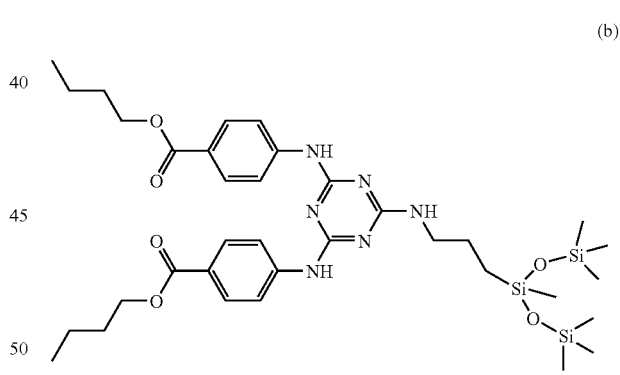

(b)

A mixture of the product from the first step of Example 1 (16.74 g, 0.0391 mol), butyl para-aminobenzoate (15 g, 0.0776 mol) and potassium carbonate (5.36 g, 0.0388 mol) was taken up in suspension in 170 ml of toluene with nitrogen bubbling through and heated under reflux for 1 hour 20 minutes. The reaction mixture was cooled and 150 ml of dichloromethane were added. The minerals were filtered. The filtrate was washed with bicarbonated water then twice with water. After drying the organic phase and evaporating off the solvents, a white powder was obtained. After recrystallization from a 1:15 EtOAc/heptane mixture, 20.1 g (yield: 69%) of the derivative of Example 2 were obtained in the form of a white powder:
MP: 110-111° C.
UV (ethanol): $\lambda_{max}$=310 nm; E1%=1020.

Example 3

Preparation of 2,4-bis(n-pentyl-4'-diylaminobenzoate)-6-{[1,3,3,3-tetramethyl-1-[(trimethylsilyl)oxy]disiloxanyl]propyl-3-ylamino}-s-triazine (c)

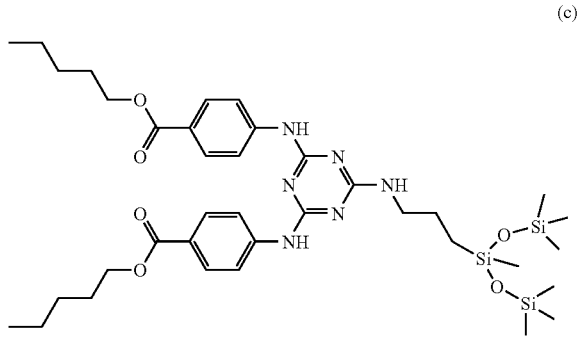 [SMILES: CCCCCOC(=O)c1ccc(Nc2nc(NCCC[Si](C)(O[Si](C)(C)C)O[Si](C)(C)C)nc(Nc3ccc(C(=O)OCCCCC)cc3)n2)cc1]

A mixture of the product from the first step of Example 1 (1 g, 2.3×10⁻³ mol), n-pentyl para-aminobenzoate (0.97 g, 4.6×10³ mol) and sodium bicarbonate (0.39 g, 4.6×10⁻³ mol) in 15 ml of toluene was heated for 20 minutes to a temperature of 115° C. in a CEM Discover microwave oven at a power of 150 watts. Dichloromethane was added to the reaction mixture and it was washed with a saturated solution of sodium chloride then twice with water. After drying the organic phase and evaporating off the solvents, a transparent oil was obtained. After purifying on a silica column (eluent: heptane/EtOAc 85:15), the fractions of the derivative of Example 3 (0.9 g; yield: 50%) were recovered in the form of a white powder:

UV (ethanol): $\lambda_{max}$=312 nm; E1%=1008.

Example 4

Preparation of 2,4-bis[(1,1,3,3-tetramethylbutyl)-4'-diylaminobenzamide]-6-{[1,3,3,3-tetramethyl-1-[(trimethylsilyl)oxy]disiloxanyl]propyl-3-ylamino}-s-triazine (d)

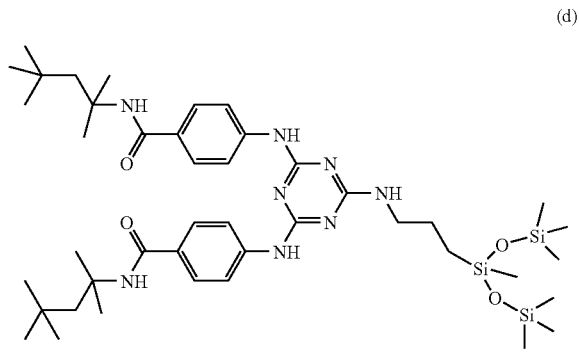 [SMILES: CC(C)(C)CC(C)(C)NC(=O)c1ccc(Nc2nc(NCCC[Si](C)(O[Si](C)(C)C)O[Si](C)(C)C)nc(Nc3ccc(C(=O)NC(C)(C)CC(C)(C)C)cc3)n2)cc1]

First Step

Preparation of 4-nitro-N-(tert-octyl)benzamide

Tert-octylamine (51.7 g, 0.4 mol) and triethylamine (61.2 ml, 0.44 mol) in 260 ml of dichloromethane were introduced into a reactor. It was heated to 70° C. then 4-nitrobenzoyl chloride (77.9 g, 0.42 mol) was added in small portions over 50 minutes. It was heated under reflux for 4 hours. The reaction mixture was poured over ice water; it was extracted with dichloromethane, dried and the solvent was evaporated off. The beige precipitate obtained was recrystallized from a mixture of isopropyl ether and ethanol (ratio 10:1). After drying under vacuum, 84.6 g (yield: 76%) of 4-nitro-N-(tert-octyl)benzamide were obtained in the form of an off-white powder and used as is in the next step.

Second Step

Preparation of 4-amino-N-(tert-octyl)benzamide 4-nitro-N-(tert-octyl)benzamide (30 g, 0.108 mol) dissolved in 200 ml of ethyl acetate was hydrogenated in a 500 ml hydrogenator in the presence of 4.8 g of palladium, 10% on charcoal with 50% water as the catalyst (hydrogen pressure: 8-10 bar) at a temperature of 70-75° C. for 1 hour and 15 minutes. After filtering, concentrating the solvent and vacuum drying, 20.4 g (yield: 76%) of 4-amino-N-(tert-octyl)benzamide were obtained in the form of a pale yellow powder and used as is in the next step.

Third Step

Preparation of Derivative of Example 4

A mixture of the product from the first step of Example 1 (1 g, 2.3×10⁻³ mol), the product from the preceding step (1.16 g, 4.6×10⁻³ mol) and sodium bicarbonate (0.39 g, 4.6×10⁻³ mol) in 10 ml of dry toluene was heated in a CEM Discover microwave oven for 20 minutes to a temperature of 115° C. at a power of 150 watts. Dichloromethane was added to the reaction mixture and it was washed with a saturated solution of sodium chloride then twice with water. After drying the organic phase and evaporating off the solvents, a pale yellow oil was obtained. After purifying on a silica column (eluent: heptane/EtOAc 70:30), the fractions of the derivative of Example 3 were recovered (0.9 g; yield: 45%) in the form of white flakes:

UV (ethanol): $\lambda_{max}$=302 nm; E1%=775.

Example 5

Preparation of 2,4-bis(methyltrimethylsilyl 4'-diylaminobenzoate)-6-{[1,3,3,3-tetramethyl-1-[(trimethylsilyl)oxy]disiloxanyl]propyl-3-ylamino}-s-triazine (e)

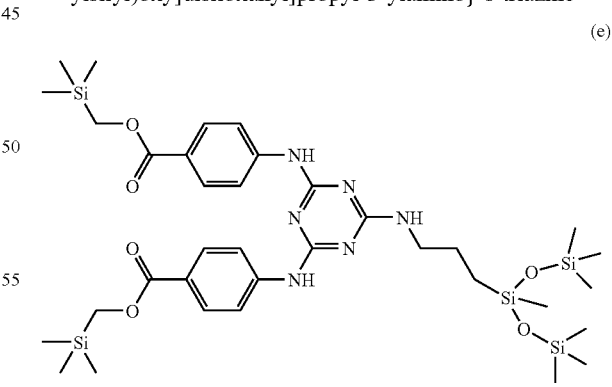

First Step

Preparation of methyltrimethylsilyl 4-aminobenzoate

Chloromethyltrimethylsilyl (38.5 g, 0.314 mol) was added dropwise at 80° C. to a heterogeneous mixture of the potassium salt of para-aminobenzoic acid (50 g, 0.285 mol) in 350 ml of DMF in a reactor. It was heated under reflux for 3 hours. After cooling, the salts were filtered and the DMF was evaporated off. The residue was taken up in dichloromethane, dried and the solvent was evaporated off. The oil obtained was purified by distillation. Fractions were recovered which distilled at 189° C. in a vacuum of 0.6 mbar. The oil crystallized out. 50.4 g (yield: 79%) of the derivative of Example 5 were obtained in the form of a white powder and used as is in the next step.

Second Step

Preparation of Derivative of Example 5

A mixture of the product from the first step of Example 1 (2.1 g, 4.9×10$^{-3}$ mol) and the derivative from the preceding step (2.19 g, 9.8×10$^{-3}$ mol) in 40 ml of toluene was heated under reflux for 5 hours with nitrogen bubbling through. It was cooled and the solvent was evaporated off. The residue was taken up in dichloromethane, dried and the solvent was evaporated off. 3 g (yield: 76%) of the derivative of Example 5 were obtained in the form of a pale yellow gum:

UV (ethanol): $\lambda_{max}$=311 nm; E1%=907.

Example 6

Preparation of 2,4-bis(2-ethylhexyl 2'-hydroxy-4'-diylaminobenzoate)-6-{[1,3,3,3-tetramethyl-1-[(trimethylsilyl)oxy]disiloxanyl]propyl-3-ylamino}-s-triazine (f)

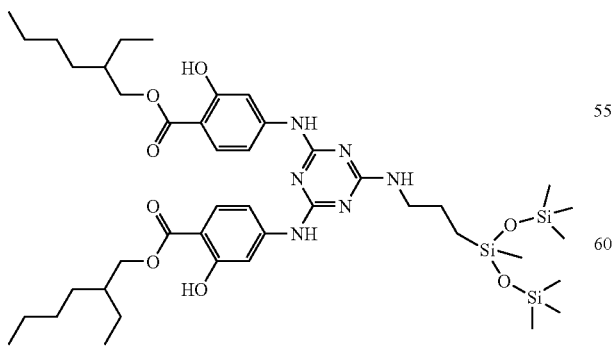

A mixture of 2-ethylhexyl 2-hydroxy-4-aminobenzoate (1.4 g, 5.57×10$^{-3}$ mol) and the product from the first step of Example 1 (1.19 g, 2.78×10$^{-3}$ mol) in 10 ml of toluene was heated under reflux for 5 hours with nitrogen bubbling through. It was cooled and the solvent was evaporated off. The residue was chromatographed on a silica column (eluent: heptane/EtOAc 9:1). 1.58 g (yield: 64%) of the fractions of the derivative of Example 6 were obtained in the form of a white paste:

| UV (ethanol): | $\lambda$ = 300 nm; | E1% = 480 |
| | $\lambda_{max}$ = 325 nm; | E1% = 709. |

Example 7

Preparation of Random Derivative of Formula (1a):
$R_1$=butyl, X=O, n=0, B=A, W=H, Z=CH$_2$, $R_7$=CH$_3$, s=0, r=8.1

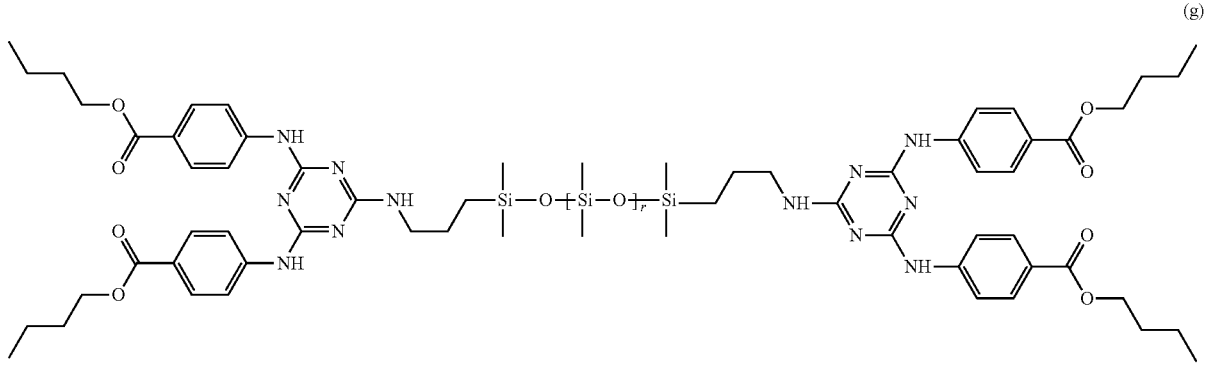

(g)

First Step

Preparation of 2,4-bis(n-butyl-4'-diylaminobenzoate)-6-chloro-s-triazine n-Butyl para-aminobenzoate (113.94 g, 0.59 mol) and a potassium carbonate solution (40.68 g, 0.295 mol) in 50 ml of water were simultaneously added dropwise at 5° C. to a solution of cyanuryl chloride (54.36 g, 0.295 mol) in 500 ml of dioxane and 50 ml of water so that the pH was from 3 and 6.5. It was kept at 5° C. for 1 hour 30 minutes. A precipitate formed in the medium which corresponded to the monosubstituted s-triazine. It was heated steadily to 70° C. and the second equivalent of potassium carbonate (40.68 g, 0.295 mol) was added in 50 ml of water. Stirring was then maintained for 5 hours at 70° C. The reaction mixture was cooled and filtered. The precipitate formed was washed with water, drained and dried. After recrystallizing from dioxane/water, after vacuum drying, 52.5 g (yield: 36%) of 2,4-bis(n-butyl-4'-diylaminobenzoate)-6-chloro-s-triazine were obtained from the first recrystallization in the form of a white powder after vacuum drying.

Second Step

Preparation of Derivative of Example 7

A mixture of the preceding product (2 g, 4×10$^{-3}$ mol), aminopropyl terminated polydimethylsiloxane (DMS-A-11 from Gelest) (2.13 g, 2×10$^{-3}$ mol) and pyridine (0.32 ml, 4×10$^{-3}$ mol) in 40 ml of toluene was heated to 70° C. for 5 hours with nitrogen bubbling. It was cooled, dichloromethane was added and the organic phase was washed 3 times with water. After drying the organic phase and evaporating off the solvents, a brown oil was obtained. After treatment with carbon black in hot ethanol and filtering over Celite, 3.3 g (yield: 70%) of the derivative of Example 7 were obtained in the form of a light brown gum:

| UV (ethanol): | $\lambda_{max}$ = 311 nm; | E1% = 916. |

Example 8

Preparation of butyl 4-{[4-{[4-(butoxycarbonyl)phenyl]amino}-6-({3-[diethoxy(methyl)silyl]propyl}amino)-1,3,5-triazine-2-yl]amino}benzoate

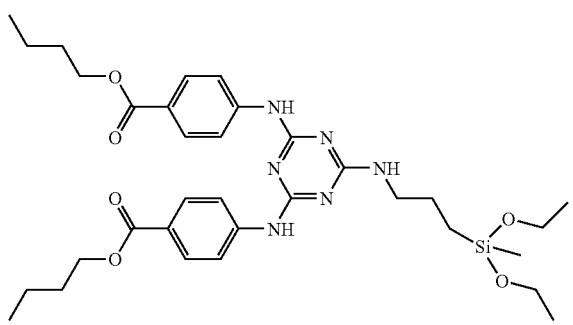

(i)

A heterogeneous mixture of the product from the first step of Example 7 (20 g, 0.04 mol) and aminopropyl diethoxymethylsilane (15.37 g, 0.08 mol) was heated steadily to 70° C. with nitrogen bubbling through. After one hour, it was cooled, dichloromethane was added and the organic phase was washed 3 times with water. After drying the organic phase and evaporating off the solvents then recrystallizing from heptane, 21 g (yield: 80%) of a white solid of the derivative of Example 8 were obtained:

| UV (ethanol): | $\lambda_{max}$ = 311 nm; | E1% = 1197. |

Example 9

Preparation of Random Derivative of Formula (1a) obtained by polymerization of derivative of Example (8) with D5+MM: $R_1$=n-butyl, X=O, n=0, W=H, a=1, b=2, R=CH$_3$, Z=CH$_2$

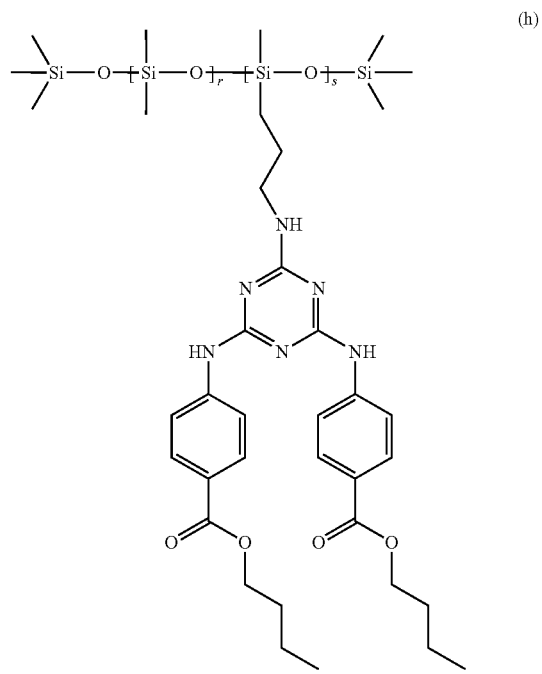

(h)

A heterogeneous mixture of the product of Example 8 (1 g, 1.53×10$^{-3}$ mol), decamethylcyclopentasiloxane (D5) (0.57 g, 1.53×10$^{-3}$ mol), hexamethyldisiloxane (MM) (0.062 g, 0.38× 10$^{-3}$ mol) and concentrated hydrochloric acid (0.1 ml) was vigorously stirred with nitrogen bubbling through in a mixture of 10 ml of toluene and 1 ml of water. It was heated steadily to 70° C. and left at this temperature for 2 hours. After cooling to ambient temperature and diluting with water, the whole medium was filtered. The precipitate obtained was washed with water and dried. 0.56 g of a white powder of the derivative of Example 9 was obtained:

| UV (ethanol): | $\lambda_{max}$ = 311 nm; | E1% = 892. |

FORMULATION EXAMPLES

The following oil/water emulsions were produced; the quantities are expressed as percentages by weight with respect to the total weight of each composition.

| | Composition | | |
|---|---|---|---|
| | Formula 1 | Formula 2 | Formula 3 (not in accordance with the invention) |
| Phase A | | | |
| Poly Dimethylsiloxane | 0.5 | 0.5 | 0.5 |
| Preservatives | 1 | 1 | 1 |

|  | Composition | | |
|---|---|---|---|
|  | Formula 1 | Formula 2 | Formula 3 (not in accordance with the invention) |
| Stearic acid | 1.5 | 1.5 | 1.5 |
| Glyceryl monostearate/PEG stearate (100 OE) mixture | 1 | 1 | 1 |
| Mixture of cetylstearyl glucoside and cetyl, stearyl alcohols | 2 | 2 | 2 |
| Cetyl alcohol | 0.5 | 0.5 | 0.5 |
| 4-tertiobutyl-4'-methoxy-dibenzoylmethane | 2 | 2 | 2 |
| Benzoate of C12/C15 alcohols | 10 | 10 | 10 |
| 2,4-bis(n-butyl 4'-diylaminobenzoate)-6-{[1,3,3,3-tetramethyl-1-[(trimethylsilyl)oxy]disiloxanyl]-propyl-3-ylamino}-s-triazine | 2 | 4 | — |
| Phase B | | | |
| Deionized water | QS 100 | QS 100 | QS 100 |
| Complexing agent | 0.1 | 0.1 | 0.1 |
| Glycerol | 5 | 5 | 5 |
| Xanthan gum | 0.2 | 0.2 | 0.2 |
| Monocetyl phosphate | 1 | 1 | 1 |
| Phase C | | | |
| Isohexadecane | 1 | 1 | 1 |
| Acrylic acid/stearyl methacrylate copolymer | 0.2 | 0.2 | 0.2 |
| Triethanolamine | QS pH | QS pH | QS pH |

Mode of Operation:

The aqueous phase (phase B) containing all of its ingredients was heated to 80° C. on a water bath. The fatty phase (phase A) containing all of its ingredients was heated to 80° C. on a water bath. A was emulsified into B using a rotor-stator agitator (a device marketed by Moritz). Phase C was incorporated and it was allowed to return to ambient temperature with moderate stirring. Triethanolamine was introduced to adjust the pH to the desired value at the end of fabrication.

Measurement Method:

For each formula, 3 test samples and 3 reference samples were prepared. 2 mg/cm² of formula were deposited onto polymethylmethacrylate plates using a spatula.

The test plates were exposed for 37 min in a SUN TEST HERAUS provided with a Xenon lamp having a UV-A flux of $9.68 \cdot 10^{-3}$ W/cm² and a UV-B flux of $5.76 \cdot 10^{-4}$ W/cm².

The reference plates were kept for the same period at the same temperature (38-40° C.) in darkness.

At the end of this period, the filters were extracted by immersing each plate in 50 g of methanol and subjecting them to ultrasound for 15 minutes to ensure proper extraction. The solutions obtained were analyzed by HPLC and UV spectrophotometry.

For each test formula, the amount of residual 4-tertiobutyl-4'-methoxy-dibenzoylmethane after exposure was given by the ratio of its optical density (OD) in the exposed sample to its unexposed optical density (OD). The absorption maximum corresponding to butyl-methoxydibenzoylmethane was used: $\lambda_{max}=358$ nm.

The results obtained are summarized in the following table:

| Compositions | Residual % of dibenzoylmethane after exposure |
|---|---|
| Formula 1 | 56 ± 3% |
| Formula 2 | 65 ± 4% |
| Formula 3 (not in accordance with invention) | 25 ± 4% |

Formulations 1 and 2, in accordance with the invention, containing 4-tertiobutyl-4'-methoxy-dibenzoylmethane combined with a compound of formula (1) (i.e., 2,4-bis(n-butyl 4'-diylaminobenzoate)-6-{[1,3,3,3-tetramethyl-1-[(trimethylsilyl)oxy]disiloxanyl]propyl-3-ylamino}-s-triazine) were substantially more photostable than formulation 3 containing 4-tertiobutyl-4'-methoxy-dibenzoylmethane alone.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A topically applicable UV-photostabilized cosmetic/dermatological composition comprising at least one dibenzoylmethane compound screening agent and at least one compound having structural unit (b) below, or a tautomeric form thereof:

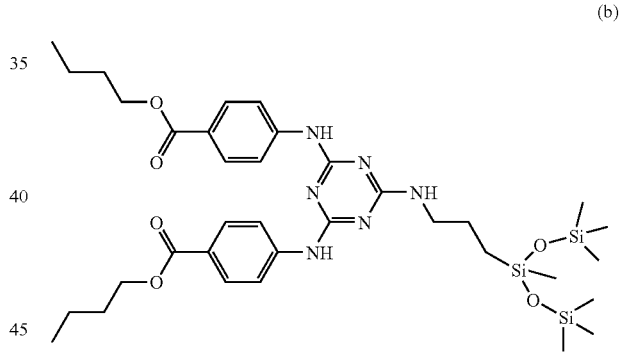

(b)

wherein the at least one dibenzoylmethane compound is/are present in amounts of 0.01% to 6% by weight with respect to the total composition weight and is/are selected from the group consisting of:
2-methyldibenzoylmethane;
4-methyldibenzoylmethane;
4-isopropyldibenzoylmethane;
4-tert-butyldibenzoylmethane;
2,4-dimethyldibenzoylmethane;
2,5-dimethyldibenzoylmethane;
4,4'-diisopropyldibenzoylmethane;
4,4'-dimethoxydibenzoylmethane;
4-tert-butyl-4'-methoxydibenzoylmethane;
2-methyl-5-isopropyl-4'-methoxydibenzoylmethane;
2-methyl-5-tert-butyl-4'-methoxydibenzoylmethane;
2,4-dimethyl-4'-methoxydibenzoylmethane; and
2,6-dimethyl-4-tert-butyl-4'-methoxydibenzoylmethane;
wherein the structural unit (b) is present in amounts of 0.01% to 6% by weight with respect to the total composition weight.

2. The cosmetic/dermatological composition as defined by claim 1, wherein the at least one dibenzoylmethane compound is 4-(tert-butyl)4'-methoxydibenzoylmethane.

3. The cosmetic/dermatological composition as defined by claim 1, further comprising other organic or inorganic photoprotective agents that are active in the UV-A and/or UV-B range and that are water-soluble or liposoluble or insoluble in the conventional cosmetic solvents.

4. The cosmetic/dermatological composition as defined by claim 3, comprising additional organic photoprotective agents selected from the group consisting of anthranilates; cinnamic derivatives; salicylic derivatives; camphor derivatives; benzophenone derivatives; [3,[3-diphenylacrylate derivatives; triazine derivatives; benzotriazole derivatives; benzalmalonate derivatives; benzimidazole derivatives; imidazolines; bis(benzoazolyl) derivatives; p-aminobenzoic acid (PABA) derivatives; methylene bis(hydroxyphenylbenzotriazole) derivatives; benzoxazole derivatives; screening polymers and screening silicones; α-alkylstyrene-derived dimers; 4,4-diarylbutadienes, and mixtures thereof.

5. The cosmetic/dermatological composition as defined by claim 4, comprising additional organic UV screening agent(s) selected from the group consisting of:
Ethylhexyl Methoxycinnamate;
Homosalate;
Ethylhexyl Salicylate;
Octocrylene;
Phenylbenzimidazole Sulfonic Acid;
Benzophenone-3;
Benzophenone-4;
Benzophenone-5;
n-Hexyl 2-(4-diethylamino-2-hydroxybenzoyl)benzoate;
4-Methylbenzylidene camphor;
Terephthalylidene Dicamphor Sulfonic Acid;
Disodium Phenyl Dibenzimidazole Tetrasulfonate;
Methylene bis-Benzotriazolyl Tetramethylbutylphenol;
Ethylhexyl triazone;
Bis-Ethylhexyloxyphenol Methoxyphenyl Triazine;
Diethylhexyl Butamido Triazone;
2,4,6-Tris(dineopentyl 4'-aminobenzalmalonate)-s-triazine;
2,4,6-Tris(diisobutyl 4'-aminobenzalmalonate)-s-triazine;
2,4,6-Tris(biphenyl-4-yl-1,3,5-triazine);
2,4,6-Tris(terphenyl)-1,3,5-triazine;
Drometrizole Trisiloxane;
Polysilicone-15;
Dineopentyl 4'-methoxybenzalmalonate
1,1-Dicarboxy-(2,2'-dimethylpropyl)-4,4-diphenylbutadiene;
2,4-Bis[5-1(dimethylpropyl)benzoxazol-2-yl-(4-phenyl)-imino]-6-(2-ethylhexyl)-imino-1,3,5-triazine; and mixtures thereof.

6. The cosmetic/dermatological composition as defined by claim 3, further comprising treated or untreated metal oxide pigments.

7. The cosmetic/dermatological composition as defined by claim 6, said pigments comprising treated or untreated titanium, zinc, iron, zirconium or cerium oxides and mixtures thereof.

8. The cosmetic/dermatological composition as defined by claim 1, further comprising at least one artificial tanning and/or browning agent for the skin.

9. The cosmetic/dermatological composition as defined by claim 1, further comprising at least one adjuvant selected from the group consisting of fatty substances, organic solvents, ionic or non-ionic, hydrophilic or lipophilic thickeners, demulcents, humectants, opacifiers, stabilizers, emollients, silicones, anti-foaming agents, fragrances, preservatives, anionic, cationic, non-ionic, zwitterionic or amphoteric surfactants, active agents, fillers, polymers, propellants, and basifying or acidifying agents.

10. The cosmetic/dermatological composition as defined by claim 1, formulated as an oil-in-water or water-in-oil emulsion.

11. The cosmetic/dermatological composition as defined by claim 1, formulated as a product for the cosmetic treatment of the skin, lips, nails, hair, eyelashes, eyebrows, and/or scalp.

12. The cosmetic/dermatological composition as defined by claim 1, formulated as a care product for the skin, lips, nails, hair, and/or scalp.

13. The cosmetic/dermatological composition as defined by claim 1, formulated as a makeup product.

14. A regime or regimen for photoprotecting a keratinous substrate against the damaging effects of UV-radiation, comprising topically applying thereon a thus effective amount of the cosmetic/dermatological composition as defined by claim 1.

15. A regime or regimen for photoprotecting the skin, hair, lips, scalp, nails, eyelashes and/or eyebrows against the damaging effects of UV-radiation, comprising topically applying thereon a thus effective amount of the cosmetic/dermatological composition as defined by claim 1.

* * * * *